(12) United States Patent
D'Africa et al.

(10) Patent No.: US 6,766,192 B1
(45) Date of Patent: Jul. 20, 2004

(54) DEVICE FOR IONTOPHORETIC TRANSCUTANEOUS ADMINISTRATION OF MOLECULES

(76) Inventors: Antonino D'Africa, Via Modena S. Sperato II Trav. 46, 89100 Reggio Calabria (IT); Guido Paduano, Via Roma 12, 22067 Missaglia Lecco (IT); Massimo Sartori, Via del Faggio 22, 22060 Carimate Como (IT)

( * ) Notice: Subject to any disclaimer, the term of this patent is extended or adjusted under 35 U.S.C. 154(b) by 0 days.

(21) Appl. No.: 09/937,511

(22) PCT Filed: Mar. 20, 2000

(86) PCT No.: PCT/IT00/00092
§ 371 (c)(1),
(2), (4) Date: Nov. 26, 2001

(87) PCT Pub. No.: WO00/56400
PCT Pub. Date: Sep. 28, 2000

(30) Foreign Application Priority Data
Mar. 22, 1999 (IT) .......................................... FI99A0055

(51) Int. Cl.[7] ................................................. A61N 1/30

(52) U.S. Cl. ......................................................... 604/20
(58) Field of Search .............................. 604/20, 21, 19; 606/32, 34, 41; 607/1, 2, 157, 153; 601/15–20; 401/208, 209

(56) References Cited

U.S. PATENT DOCUMENTS 3,163,166 A * 12/1964 Brant et al. .................... 604/20
6,385,487 B1 * 5/2002 Henley ......................... 604/20

FOREIGN PATENT DOCUMENTS

| EP | 0292930 | 11/1988 |
| FR | 1476657 | * 3/1967 |
| GB | 2195296 | 4/1988 |

* cited by examiner

Primary Examiner—Brian L. Casler
Assistant Examiner—Matthew DeSanto
(74) Attorney, Agent, or Firm—McGlew and Tuttle, P.C.

(57) ABSTRACT

The device comprises, in combination, a container (1) for the product to be administered; a dispensing element (7) through which said product is dispensed; and energy supply component (9) located adjacent to said dispensing element.

12 Claims, 3 Drawing Sheets

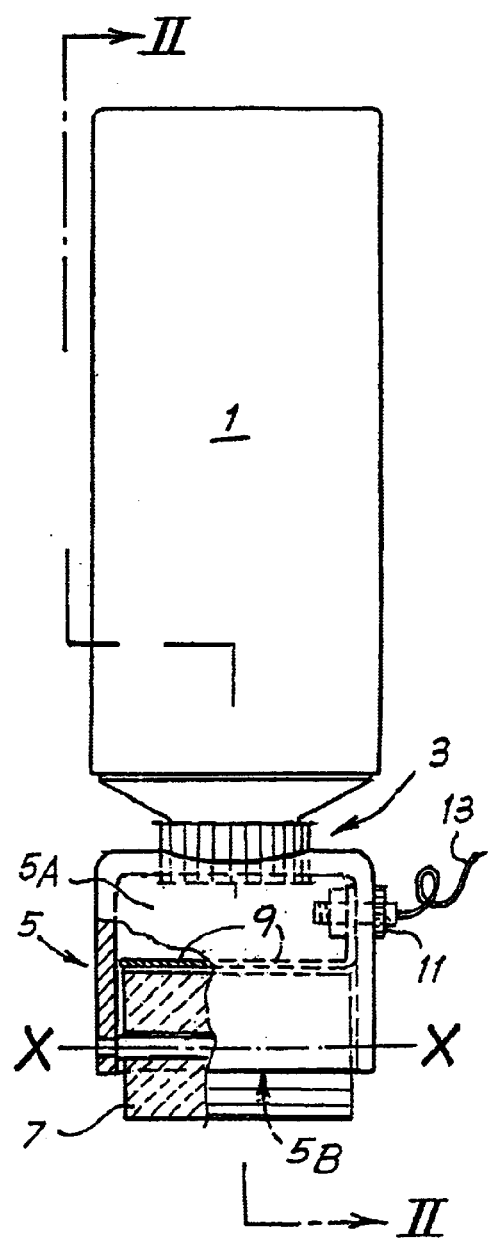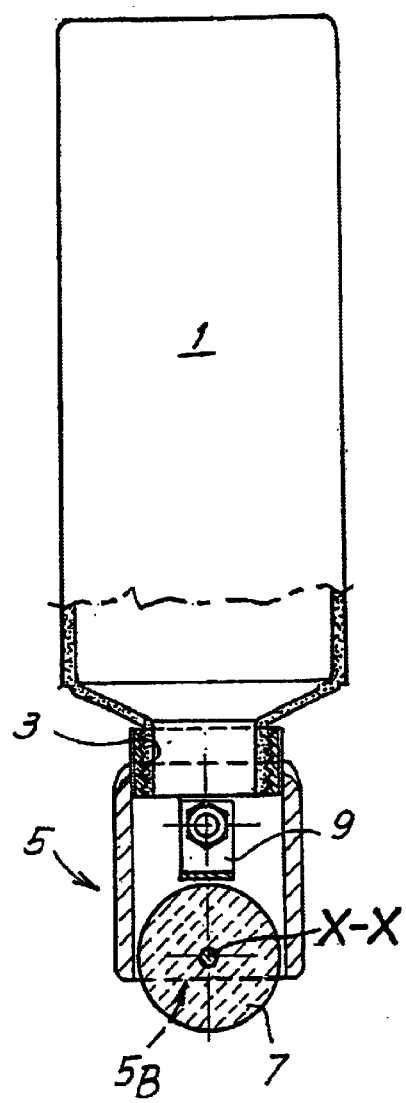

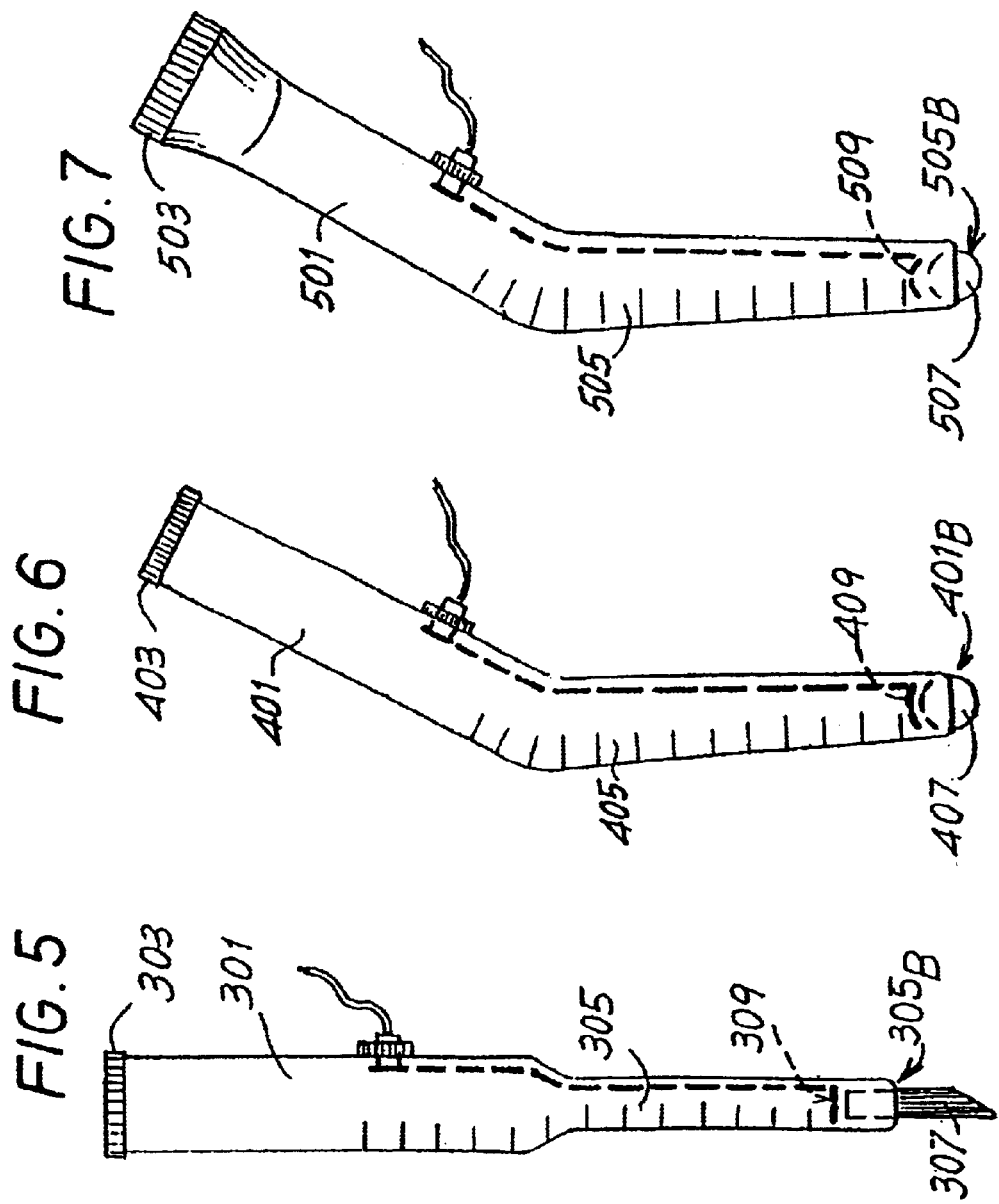

DEVICE FOR IONTOPHORETIC TRANSCUTANEOUS ADMINISTRATION OF MOLECULES

TECHNICAL FIELD

The present invention relates to a container for a suspension in gel of molecules of a medicine, a herbal remedy, a homeopathic or cosmetic product, carbon dioxide, oxygen, or nitrogen to be transported, or of other molecules or substances to be administered by iontophoresis, or by other methods requiring the application of energy which promotes the penetration of the molecules to be transported through the epidermis and beyond the cutaneous barrier of the skin.

PRIOR ART

Iontophoresis as a method of transcutaneous administration of medicines or other products for various purposes is known. This method can be used to place ionizable molecules of a substance to be transported in a container and then to bring one part of the container into contact with the skin of the patient to whom the substance is to be administered. In the part to be brought into contact with the skin, the container is closed by an osmotic or partially permeable membrane. The patient and the container in which the molecules to be transported are kept are connected in an electrical circuit with a source of voltage and/or frequency which can be varied in a controlled way, which causes the ionization of the molecules and the migration of the ions through the osmotic membrane and through the patient's skin and consequently their entry into the tissues lying under the epidermis, to a depth determined by the frequency applied. The circuit is completed by means of one or more electrodes applied to suitable parts of the body of the patient being treated.

Various kinds of iontophoresis equipment are described in the literature. For example, EP-A-0292930 describes equipment in which the container for the solution containing the molecules to be transported has an osmotic membrane through which the ions generated by the electrical field produced by a suitable apparatus migrate. The molecules are contained in liquid solution inside the container which is sealed by the osmotic membrane.

U.S. Pat. No. 5,084,008 describes a different container for the medicine to be administered by iontophoresis. In this case, the container is particularly suitable for the use of molecules to be transported which are contained in a gel, and is closed by a permeable layer which has the purpose of allowing the passage of the ions and at the same time of preventing the gel from drying out during the period for which the container is stored. The container is characterized by a particular configuration of the means of distributing the current within the medicine.

WO-8808729 describes an electrode for iontophoresis, consisting of a plate of conducting material to which is applied a porous membrane within which the molecules to be transported are placed. The membrane is protected by a removable protective sheet which is removed at the moment of application of the electrode to the patient.

WO-9622810 describes a container for a medicine to be administered by iontophoresis following the freezing of the solution containing the medicine. In this case, the container is made in two portions joined together in a reversible way and forming an internal volume in which the solution containing the medicine to be administered is placed. The container with its contents is then frozen, and at the moment of use the upper part of the container is removed to expose a block formed by the frozen solution. This block is brought into contact with the patient's epidermis. The part of the container which is not removed, and in which the base of the block of frozen solution continues to be housed, contains the electrode which has a shape suitable for providing electrical contact with the frozen block of solution.

This container has considerable drawbacks, due to the lack of arrangements for reliably fixing the two portions of the container to each other when the container has to be filled with the solution containing the medicine, the lack of a suitable seal to ensure the hygiene of the product, since the container is open at the top to allow filling, and the impossibility of ensuring that the container is used once only for reasons of hygiene. Furthermore, this container is suitably solely and exclusively for the application of previously frozen solutions. The application of the electrode is insecure and it can easily be immersed as a result of the melting of the block of ice, with the risk of electrical discharges.

Other known methods of administration of active principles through the epidermis require the use of forms of energy other than electrical energy. For example, it is known that an active principle can be made to pass through the epidermis by irradiation with a laser, and particularly with a diode laser. Another method may require administration by means of ultrasound, by means of infrared radiation, or by other means.

In the present description, reference will be made in general terms to a source of energy and to means for directing this energy toward the solution containing the molecules to be transported. This wording is to be understood as denoting any system which enables active principles or molecules of any type to be administered by a transcutaneous route by means of the supply of energy in any form.

Within the present description, reference will be made specifically to iontophoresis, as a particularly advantageous method of administration. However, this is to be considered as an indication of a preferred, but not exclusive, form of application of the present invention.

OBJECTS AND BRIEF DESCRIPTION OF THE INVENTION

The object of the present invention is to provide a container for a carrier product of relatively high viscosity, such as a gel or the like, containing molecules to be transported by iontophoresis, which overcomes the drawbacks and limitations of the conventional containers known at the present time.

More generally, the object of the present invention is to provide a container and dispenser device suitable for use with any method of administration of principles dispersed in said carrier product by the use of a source of energy. The device comprises, in combination, a container for said product;

a dispensing element through which said product is dispensed;

an energy supply component located adjacent to said dispensing element.

The container has a main body and, if necessary, a dispensing chamber where said dispensing element and said energy supply component are located, and it is also possible for said dispensing chamber to be applicable in a reversible way to the main body of the container.

Said dispensing element can be a rotating element or a piece of felt or other permeable body, and can also be formed from electrically conducting material. In this case it can be brought into electrical contact with said energy supply component, to apply an electrical potential directly to the epidermis.

The container can have a tapered portion at whose end said dispensing element and said supply component are located, and/or can have walls which are at least partly flexible, to enable pressure to be applied manually to the contents of the device to facilitate dispensing.

BRIEF DESCRIPTION OF THE DRAWINGS

The invention will be more clearly understood from the description and the attached drawing, which shows a non-restrictive example of the invention. In the drawing, FIG. 1 shows a lateral view of a device according to a first embodiment of the invention, in partial cross section;

FIG. 2 shows another lateral view of the device of FIG. 1, in section through the plane II—II; and FIGS. 3 to 7 show corresponding lateral views of devices according to other embodiments of the invention.

DETAILED DESCRIPTION OF THE PREFERRED EMBODIMENTS

Figure 4:
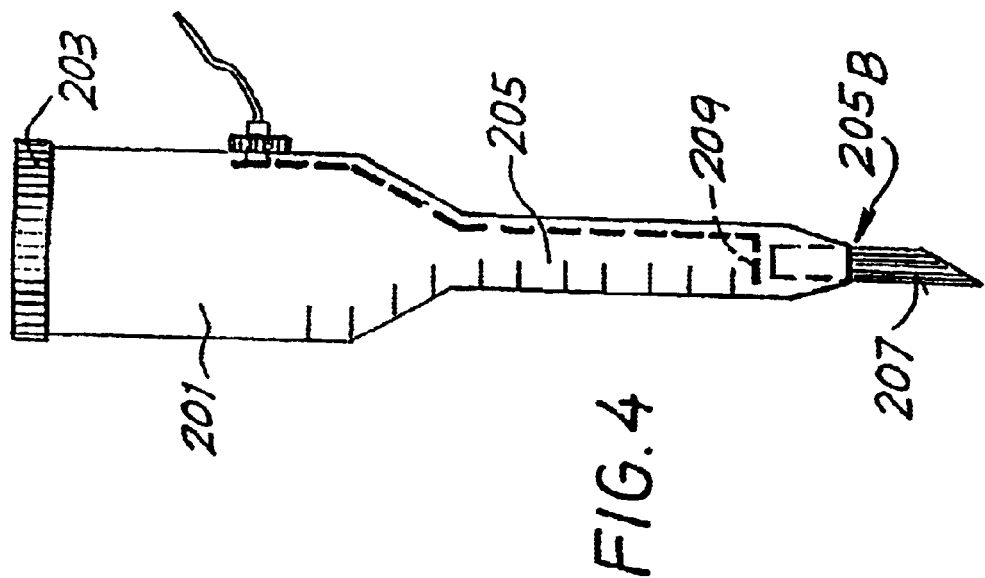

With reference to FIGS. 1 and 2, the device comprises a cylindrical container 1 having a threaded mouth 3 for a dispensing element 5 forming a dispensing chamber 5A. This dispensing chamber communicates with the container 1 and has a rectangular aperture 5B which in practice is closed, except for a minimal gap, by a roller 7 rotatable about its own axis X—X with respect to the dispensing element 5. Inside the chamber 5 there is fixed a metal bracket 9 which extends for the most in the proximity of the cylindrical surface of the roller 7 and to which an electrical potential can be applied by means of a terminal 11 and a flexible electrical conductor 13, the conductor being connected to a suitable source of electrical energy.

When a curative or other product dispersed in a carrier of high viscosity, for example a gel, has been placed in the container, the device can also be inverted into the position shown in FIGS. 1 and 2. After the terminal 11 has been connected to the electrical energy source, the device can be applied to a part of the body of a patient by making the roller 7 roll on said part. Thus the roller, which normally prevents the free exit of the viscous contents of the container 1, spreads on said part a thin layer of said carrier with the curative product activated by means of said supply of energy.

Figure 3:
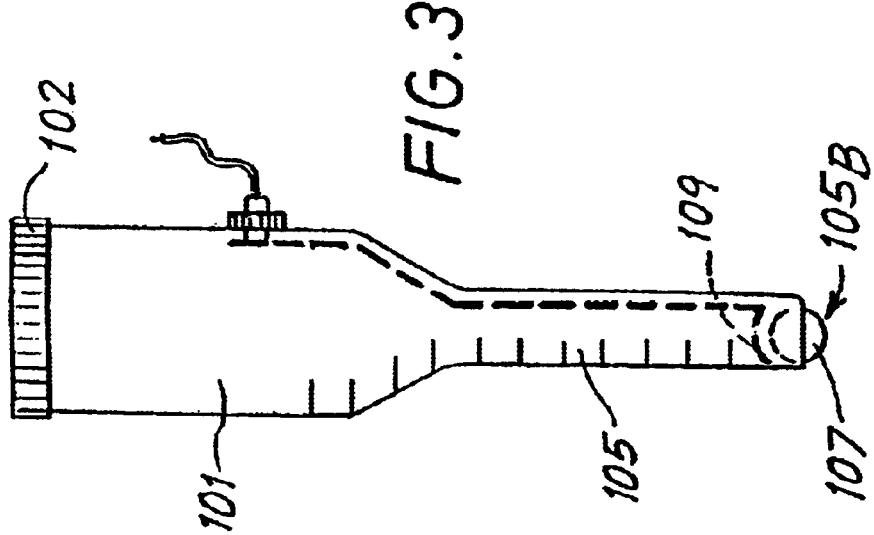

FIGS. 3 to 7 show similar devices in which the container 101, 201, 301, 401 is filled through a base aperture 103, 203, 303, 403, 503 respectively, which can be reclosed by means of a screw cap or a cap which is snap-fitted on to the body of the container, or, in the case of FIG. 7, by the lateral compression of the edge of the aperture and sealing, as is done with a tube of toothpaste. In the last case, the device is clearly disposable, since the filling can be conveniently carried out once only. Each of said devices has a dispensing chamber 105, 205, 305, 405, 505 whose diameter is reduced or tapered toward the dispensing outlet 105B, 205B, 305B, 405B, 505B in such a way as to permit treatment by iontophoresis even in restricted cavities, such as the mouth. Additionally, the devices shown in FIGS. 3 and 6 have corresponding dispensing elements 107, 407, 507 in the form of a roller or ball, as in the case of FIGS. 1 and 2, while the devices of FIGS. 4 and 5 have corresponding dispensing elements 207, 307 in the form of pieces of felt permeable by the carrier medium and cut in a wedge shape. All the illustrated devices comprise an energy supply component in the form of a strip 109, 209, 309, 409, 509 connectable by means of a conductor to a source of electrical energy. The application is similar to that described for the case of FIG. 1.

The dispensing elements 7, 107, 207, 307, 407, 507 can be formed from electrically conducting material and connected electrically to the corresponding energy supply components 9, 109, 209, 309, 409, 509. By using energy at a sufficiently low potential to prevent harm to the patient, this energy can thus be discharged directly into the patient's epidermis through the film of administered product.

In each of the embodiments of the invention described above, the container (1, 101, 201, 301, 401, 501) can have thin flexible plastic walls to enable pressure to be exerted manually on the contents during application, thus promoting its dispensing.

It is to be understood that the drawing shows only an example provided solely as a practical demonstration of the invention, and that this invention can vary in its forms and arrangements without departing from the scope of the guiding principle of the invention. The presence of any reference numbers in the attached claims has the purpose of facilitating the reading of the claims with reference to the description, and does not limit the scope of protection represented by the claims.

What is claimed is:

1. Device for the transcutaneous administration of molecules the device comprising, in combination, a container having a carrier product gel including the molecules to be administered;

a dispensing chamber detachably connected to said container and defining an intake aperture for receiving the carrier product gel from said container, said dispensing chamber defining a dispensing aperture;

a dispensing element arranged in said dispensing aperture and through which the carrier product is dispensed, said dispensing aperture being directly closed by said dispensing element, said dispensing element being a rotating element;

an electrode associated to said dispensing element, said electrode being supported in said dispensing chamber directly adjacent to said dispensing element;

a direct fluid connection between said container and said dispensing chamber.

2. Device according to claim 1, in which said container has walls which are at least partly flexible.

3. Device according to claim 2, in which said container is disposable and has its filling aperture closed by lateral compression like a tube of toothpaste.

4. Device according to claim 1, in which said container has a tapered portion at whose end said dispensing element and said electrode are located.

5. Device according to claim 1, in which said dispensing element is formed from electrically conducting material and is electrically connected to said electrode.

6. An arrangement in accordance with claim 1, wherein:

said electrode is detachable from said container along with said dispensing chamber.

7. A device in accordance with claim 1 wherein:
said container is electrically insulated from said electrode.

8. A device in accordance with claim 1, wherein:
said dispensing element is a rotating element dispensing the gel onto the patient by rolling;
said rotating element directly closes said discharge aperture.

9. A transcutaneous gel dispensing arrangement comprising:
- a container with gel to be administered to a patient, said container having an aperture and a first connection part at one end;
- a dispensing chamber defining an intake aperture and a discharge aperture, said intake aperture having a second connection part connected to said first connection part, said first and second connection part defining a passage for the gel to flow from said container to said dispensing chamber;
- a rotating dispensing element rotatably arranged in said discharge aperture for dispensing the gel onto the patient by rolling;
- an electrode arranged in said dispensing chamber, said electrode and said dispensing chamber defining a direct fluid connection between said container and said dispensing element for moving the gel from said container to said dispensing element.

10. An arrangement in accordance with claim 9, wherein:
said container is electrically insulated from said electrode;
said electrode is spaced from said container.

11. An arrangement in accordance with claim 9, wherein:
said rotating element directly closes said discharge aperture.

12. A transcutaneous gel dispensing arrangement comprising:
- a container for holding gel to be administered to a patient, said container having an aperture and a first connection part at one end;
- a dispensing chamber defining an intake aperture and a discharge aperture, said intake aperture having a second connection part connected to said first connection part, said first and second connection part defining a passage for the gel to flow from said container to said dispensing chamber;
- a rotating dispensing element rotatably arranged in said discharge aperture for dispensing the gel onto the patient by rolling;
- an electrode arranged in said dispensing chamber, said electrode and said dispensing chamber defining a direct fluid connection between said container and said dispensing element for moving the gel from said container to said dispensing element, said container being electrically insulated from said electrode.

* * * * *